United States Patent [19]

Bigbee et al.

[11] Patent Number: 4,767,710

[45] Date of Patent: * Aug. 30, 1988

[54] CELL LINES FOR THE PRODUCTION OF MONOCLONAL ANTIBODIES TO HUMAN GLYCOPHORIN A

[75] Inventors: William L. Bigbee, Livermore; Stella S. N. Fong, Del Mar; Ronald H. Jensen, Livermore; Martin Vanderlaan, San Ramon; Richard G. Langlois, Livermore, all of Calif.

[73] Assignee: The United States of America as represented by the United States Department of Energy, Washington, D.C.

[*] Notice: The portion of the term of this patent subsequent to Jun. 21, 2005 has been disclaimed.

[21] Appl. No.: 734,312

[22] Filed: May 15, 1985

Related U.S. Application Data

[63] Continuation of Ser. No. 450,694, Dec. 17, 1982, abandoned.

[51] Int. Cl.[4] .............. C12N 5/00; C12N 15/00; C12P 21/00; C07K 15/04
[52] U.S. Cl. .............. 435/240.27; 435/172.2; 435/68; 935/95; 935/103; 350/387
[58] Field of Search ............ 435/7, 68, 172.2, 240, 435/241, 948; 436/547, 548; 935/89, 90, 93, 95, 103, 102, 106, 110; 530/387

[56] References Cited

U.S. PATENT DOCUMENTS 4,271,145 6/1981 Wanos ................. 435/240 X

OTHER PUBLICATIONS

Edwards, P., *Biochem Soc. Trans.* vol. 9, pp. 334–335 (1980).
Anstee, D. et al, *Eur. J. Immunol.*, vol. 12, pp. 228–232 (1982).
Boumsell, L. et al, *J. Immunolog. Methods*, vol. 38, pp. 225–229 (1980).
Noonan, K. et al., in *Monoclonal Antibodies in Endocrine Res.* (Eds. Fellows & Eisenbarth) pp. 41–52 (1981).
Springer, G. et al., *Immunochemistry*, vol. 14, pp. 497–502 (1977).
Anstee, D. in *Monoclonal Antibodies in Clin. Med.* (Eds. McMichael & Fabre) pp. 237–249 (1982).

*Primary Examiner*—Thomas G. Wiseman
*Assistant Examiner*—Jayme A. Huleatt
*Attorney, Agent, or Firm*—Berthold J. Weis; L. E. Carnahan; Judson R. Hightower

[57] ABSTRACT

Cloned mouse hybridoma cell lines have been established which continuously produce antibodies that differentiate between the M and N forms of human glycophorin A. These antibodies have potential application as human blood group reagents, as markers for terminally differentiated erythroid cells and as immunofluorescent labels of somatically variant human erythrocytes.

2 Claims, No Drawings

CELL LINES FOR THE PRODUCTION OF MONOCLONAL ANTIBODIES TO HUMAN GLYCOPHORIN A

The U.S. Government has rights in this invention pursuant to Contract No. W-7405-ENG-48 between the University of California and the U.S. Department of Energy.

This is a continuation of application Ser. No. 450,694 filed Dec. 17, 1982, now abandoned.

This invention relates to a method for the continuous production of monoclonal antibodies to human glycophorin A antigen and to cell lines which produce such antibodies.

BACKGROUND OF THE INVENTION

Human erythrocyte membranes have at least three electrophoretically distinguishable glycoprotein compounds. Glycoproteins are proteins conjugated with a small number of heterosaccharide prosthetic groups. Electrophoretic and immunologic analysis of erythocyte membrane glycoproteins reveal that different glycoproteins are associated with different blood group antigens (ABO, MN, S and others).

The major glycoprotein of the human red cell membrane, called glycophorin A, is a single polypeptide chain composed of one hundred and thirty-one amino acid residues and approximately one hundred and twenty-five sugar residues. Glycophorin molecules are distributed uniformly over the red cell surface and appear to be associated with the intra-membranous particles. Glycophorin A occurs in two allelic forms responsible for the MN blood group, as well as serving as a receptor for kidney bean phytohemagglutinin, wheat germ agglutinin and influenza viruses. (An allele is either of a pair of genes located at the same position on both members of a pair of chromosomes which convey inherited characteristics alternatively in accordance with Mendelian laws.)

MN is a blood group system in which two alleles identified as M and N determine the presence of corresponding antigens on the red cells and give rise to three phenotypes MM, MN and NN. Humans may be "typed" as having either the M-type (MM homozygous), or the N-type (NN homozygous) or an MN combination type (MN heterozygous) of the two genotypes on their red cells.

The two alleles, M and N, determine a difference in the amino acid sequence of glycophorin A, such that glycophorin A normally occurs in two forms, glycophorin $A^M$ and glycophorin $A^N$. Glycophorin $A^M$ differs from glycophorin $A^N$ in only two amino acid residues. Serine and glycine are found in positions 1 and 5 of the amino acid sequence of glycophorin $A^M$ and leucine and glutamic acid replace these amino acids at the corresponding positions in glycophorin $A^N$. It has been postulated that the serological distinction between $A^M$ and $A^N$ resides within the amino terminal regions of these proteins.

Blood group typing has, up until now, been done by obtaining from rabbit antisera, antibodies (immunoglobulins) and reacting them with the blood sample to be typed. Conventionally, this is done by repeated injections of human red blood cells into the animal at two- or three-week intervals, bleeding the animal, isolating the serum and absorbing out the cross-reacting antibodies. Based on their ability to agglutinate red blood cells, clinical laboratories use this type of antisera to type blood samples. Antisera produced in this manner, typically contain polyclonal mixtures of antibodies produced by the animal in response to different antigens or to different immunologic determinants on the same antigen and include antibodies that differentiate between the two glycophorins on the basis of differences in the amino acid residues, either at the first or at the fifth position or at both positions. Antisera are not precisely defined chemical reagents and their composition, therefore, vary from lot to lot of the serum.

For some applications, this lack of specificity or precision is not crucial. For certain other applications, specific monoclonal antibodies would be a critical requirement. Monoclonal antibodies to some specific antigens have been prepared by fusing antigen-sensitized mouse spleen cells (capable of producing antibodies to the specific antigen) with mouse myeloma cells (with self-replicating characteristics both in vivo and in vitro) and cloning the hybrid myeloma cells which now produce the desired antibodies in large quantities.

However, deriving a specific hybrid myeloma that produces antibodies to a selected antige or to a specific antigenic determinant is usually fraught with difficulties as the characteristics of the hybridoma vary with the antigenic determinant unique to the antigen and with the immune response of the animal chosen. Furthermore, when the immune response is very weak, the search for a hybrid clone secreting the specific antibody among the many clones secreting nonspecific immunoglobulins present special problems and require special procedures.

Preparation of monoclonal antibodies for sheep red blood cells, by fusing a mouse spleen cell sensitized with sheep red blood cells, with a mouse myeloma cell and culturing the fused hybrid cell (hybridoma) (which now produces antibodies to sheep red blood cell antigens), in a suitable culture medium, was first reported by Milstein and Kohler in Nature, 256, 493 (1975) and in Eur. J. Immunol. 5, 720 (1975). Koprowski et al., (U.S. Pat. No. 4,196,263) disclosed a method and cell line for the production of anti-influenza antiviral antibodies and Wands et al., (U.S. Pat. No. 4,271,145) described a cell line for the production of monoclonal antibodies to hepatitis virus.

But few monoclonal antibodies have been developed or reported for blood group substance antigens or for the surface proteins of red blood cells. It would be highly desirable, therefore, to obtain monoclonal antibodies to specific blood group substances for utilization as reliable standardized reagents for accurate clinical blood-typing for transfusions and for other clinical and nonclinical uses. Monoclonal antibodies specific for the M and N form of human glycophorin A would be superior blood-typing reagents since they can be obtained in large quantities in pure form eliminating lot to lot variability and the need to absorb whole sera in order to obtain specific reagents.

SUMMARY OF THE INVENTION

It is an object of this invention, therefore, to produce monoclonal antibodies to blood group substances for use in more accurate MN blood group typing.

Another object of the present invention is to produce monoclonal antibodies to human glycophorin A.

Another object of the instant invention is to develop and propagate continuous fused hybrid cell lines (hybridomas) that produce monoclonal antibodies to human glycophorin A antigen.

Another object is to provide a method for the continuous production of monoclonal antibodies to human glycophorin A antigen.

It is a further object of the present invention to provide a method by which human erythrocyte glycophorin $A^M$ and glycophorin $A^N$ may be differentiated.

A further object is to provide a method for the production of monoclonal antibodies which differentiate between glycophorin $A^M$ and glycophorin $A^N$.

Yet another object is to isolate and propagate cell lines (hybridomas) which continuously secrete monoclonal antibodies which distinguish between glycophorin $A^M$ and glycophorin $A^N$.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the present invention is directed to the production of monoclonal antibodies to human blood group substances, more specifically, to glycophorin A. The present invention also provides a method for the production of monoclonal antibodies to human glycophorin A antigen and to hybrid cell lines capable of continuously producing these antibodies.

The method of the subject invention comprises immunizing a suitable animal with the glycophorin A antigen, obtaining from the animal sensitized spleen cells or lymphocytes capable of producing antibodies to the glycophorin A antigen, fusing the sensitized spleen cells with myeloma cells of the same species or of another animal species, culturing the hybrid cells in a culture medium, isolating colonies of hybrid cells (hybridomas) which produce specific antibodies to the antigen, and harvesting the antibodies from the culture medium or a suitable host for growing the cells.

According to a further aspect of the present invention, in accordance with its objects and purposes, the cell lines developed are capable of producing highly specific monoclonal antibodies which distinguish between the M and N forms of human glycophorin A.

The present invention provides an improved method for the differentiation between the two types of glycophorins, glycophorin $A^M$ and glycophorin $A^N$ and for more accurate blood group typing by the utilization of highly specific monoclonal antibodies. These antibodies may also prove useful as a specific marker for differentiated erythroid cells grown in vitro or occurring in vivo and characterizing erythroid leukemias.

Also the reagents have an application as immunofluorescent markers which can be used to enumerate circulating red blood cells which have the property of altered expression of the glycophorin $A^M$ or $A^N$ alleles due to somatic mutation in stem cells. Such a measurement has potential as an assay for in vivo cellular somatic mutations in man.

DETAILED DESCRIPTION OF THE INVENTION

To achieve the foregoing and further objects and in accordance with the purpose of the present invention, glycophorin A from human subjects is isolated and purified by known techniques. Laboratory animals, such as mice, rats, monkeys, rabbits or dogs, preferably mice of any suitable genetic strain, are immunized with human glycophorin A samples (containing both the M and N types) in sufficient dosages to produce a measurable immune response in the animal, preferably yielding agglutinating titers of approximately 1:100 or better. Whole red blood cells with MN determinants are administered intraperitoneally at intervals of one to three weeks, preferably two weeks. Repeated or additional dosages and/or administrations may be needed to produce the desired level of response. These dosages may vary from about 0.2 to 0.5 ml of a suspension of $10^9$ washed human erythrocytes in sterile saline or a similar physiologically compatible suspension medium. A mixture of purified glycophorin $A^M$ and $A^N$ is given intravenously for three days ( 1 mg/ml, 0.1 ml/mouse) just prior to fusion. Spleen cells, now sensitized with glycophorin A are isolated and fused with myeloma cells of the same or a different species of animal in a suitable medium. The fused cells are cloned in vitro in any suitable growth medium. Various appropriate colonies of cells are then isolated and tested for the production of the desired antibodies.

Detailed procedures for the production of monoclonal antibodies to human glycophorin A in accordance with one preferred embodiment of the present invention are provided below.

Preparation And Purification Of Glycophorin A

Blood samples were drawn, with informed consent, from healthy volunteers in the Medical Department of the Lawrence Livermore National Laboratory, Livermore, California. Human glycophorin A samples from any other source are equally suitable. These samples were then screened for ABO, Rh and MN phenotypes using commercial typing sera (Ortho Diagnostics, Raritan, NJ). Glycophorin A from homozygous M and N individuals was isolated and purified from red cell membrane preparations by a sequence of detergent solubilization, phenol extraction, ethanol precipitation and chromatography on Sepharose 6B (Pharmacia, Piscataway, N.J.) according to procedures known in the art. The purified glycoprotein was dialyzed exhaustively against distilled water, lyophilized and stored desiccated at $-20°$ C. Purity of the preparations was checked using sodium dodecasulfate (SDS) polyacrylamide gel electrophoresis. Gels containing 10% acrylamide were prepared and electrophoretic experiments were carried out in a Bio-Rad (Richmond, CA) slab gel apparatus according to routine methods employed in the art. Coomassie Blue and Periodic Acid-Schiff (PAS) staining revealed the presence of PAS-1 and PAS-2 bands characteristic of the dimer and monomer forms of glycophorin A. A small amount of glycophorin B, PAS-3, was also observed to be present.

Immunization

Six one-month-old Biozzi high-responder strain of mice were immunized by three interperitoneal (IP) injections of 2 ml of a suspension of $10^9$ washed human erythrocytes in sterile saline at approximately two-week intervals. The red cells were freshly obtained from Type O, Rh negative homozygous M and N donors. Each injection consisted of an equal mixture of the two cell types. Sera obtained by bleeding through the retroorbital plexus, were tested for anti-human red cell activity using a red cell agglutination assay as described herein below. Sera from all the six immunized animals exhibited high agglutinating titers (approximately 1:100) but none of the sera distinguished between M and N cells. Control sera from non-immunized mice were negative.

One week after the last IP injection with whole cells, each mouse was given an intravenous (IV) injection of 0.2 ml of a 500 $\mu$g/ml solution of an equal mixture of purified glycophorin A$^M$ and A$^N$ pooled from homozygous donors of various ABO and Rh phenotypes. The IV injection was repeated about three weeks later. Sera from the mice were retested using the agglutination assay, whole red cell assay and purified antigen enzyme-linked immunoabsorbant assay (ELISA), as described herein below. Sera from all six mice were positive in the three assays, indicating production of glycophorin A antibodies. The animal with the highest serum titer was selected and starting one week later, was given the same IV injection as before for three consecutive days. One day after the last injection, the spleen was removed, the spleenocytes obtained by mashing the spleen through a screen mesh and the erythrocytes hynotically lysed with a solution of 0.15M NH$_4$Cl and 25 mM Tris-HCl buffer, pH 7.5.

Cell Fusion And Cloning

The single cell suspension of spleen lymphocytes (about $10^8$ cells) was mixed with about $10^7$ log phase SP2/O myeloma cells (available from Salk Institute, La Jolla, CA). Although SP2/O myeloma cells were actually used in these experiments, any comparable, 8-azaguanine-resistant, nonsecreting myeloma cell line may be substituted. The myeloma cells were grown in supplemented Dulbecco's Modified Eagle's Medium (SDMEM) which consists of Dulbecco's Modified Essential Medium (DMEM) (Gibco, Santa Clara, CA) with 25 mM glucose, 25 mM NaHCO$_3$, 17 mM HEPES buffer (N-2 hydroxyethyl piperazine- N-2-ethane), 10 mM non-essential amino acids (Gibco), 50 $\mu$M 2-mercaptoethanol, 2 mM pyruvic acid, sodium salt, 3 mM hypoxanthine, 300 $\mu$M thymidine and 2% rabbit serum (RS, Quadroma, Escondido, CA). The cells were maintained at 37° C. in a humidified incubator with a 5% CO$_2$ atmosphere. The fusion protocol was a variation of that described by Oi and Herzberg (*Selected Methods in Cellular Immunology*, B. Mishell and S. Shiigi, eds., W. H. Freeman, San Francisco, CA), consisting of 4.75 ml polyethylene glycol (PEG 1540, Polysciences, Warrington, PA) mixed with 5 ml serum-free SDMEM, 0.75 ml dimethylsulfoxide (DMSO) and 50 $\mu$l 1 M NaOH. NaOH was used to bring the mixture to a pH of about 7.8 as measured by the phenol red in SDMEM. The spleen lymphocytes and myeloma cells were co-centrifuged and pelleted in a 50 ml conical centrifuge tube. The pellet was resuspended in 1 ml of the 50% PEG solution for a period of 1 minute. The slurry of the cells was stirred for an additional minute and then 2 ml of serum-free SDMEM was added over the next 2 minutes, followed by an additional 7 ml of serum-free SDMEM over the next two minutes. The resulting 10 ml suspension was diluted to 50 ml in SDMEM containing 2.0% RS and 1 $\mu$M aminopterin. All the solutions were pre-warmed to 37° C. and maintained at or near that temperature during fusion with the use of a 37 C Temp-Blok (American Scientific Products). Any comparable protocol using PEG or Sendai virus as a fusagen and which results in viable hybridomas that can be successfully cultured may also be used.

For cloning, 0.1 ml of the mixture per well was dispensed into five 96-well microculture plates (M. A. Bioproducts, Los Angeles, CA) containing a macrophage feeder layer. These macrophage cells were obtained from pristane (2,6,10,14-tetramethylpentadecane, Aldrich Chemical Co., Milwaukee, WI) primed Balb/c mice (Simonson, Gilroy, CA). Approximately $10^3$ peritoneal macrophages in SDMEM with 2% RS, were seeded per well and allowed to attach by overnight incubation at 37° C. prior to the fusion. On days 7, 14 and 20 following fusion, the cultures were refed with 0.1 ml of a fresh medium solution containing 40 $\mu$M aminopterin. The hybridomas were refed with aminopterin-free medium beginning on day 23. On day 20, 50 $\mu$l of medium from each well was assayed for anti-red cell antibody production using the whole red cell ELISA. Cells from the most positive wells were transferred and set up as 1.0 ml cultures in 24-well culture plates (M.A. Bioproducts, Los Angeles, CA) with an optional macrophage feeder layer of $2.5 \times 10^5$ cells/well. Supernatants from these wells were reassayed on days 23 and 29 to identify those cultures maintaining high activity and the capacity to discriminate between M and N red cells. The most promising of these were passaged to T-25 flasks and sub-cloned twice by limiting dilutions in 96-well culture plates over macrophage feeder layers. ELISAs were performed at various times during the sub-cloning to assure continued antibody production of the specificity originally identified.

Four sets of clones were isolated and cultured further. They are on deposit with the American Type Culture Collection, Bethsda, MD and are assigned ATCC Accession numbers HB8159, HB8160, HB8161 and HB8162. The HB8160 and HB8159 hybridomas reacted with glycophorin A$^M$ but not with A$^N$. The HB8161 hybridoma reacted with glycophorin A$^N$ but not with A$^M$. The HB8162 hybridoma reacted with both M and N forms of glycophorin A.

Stocks of sub-cloned cells were frozen in freezing media consisting of about 70% SDMEM, 20% heat inactivated fetal calf serum, and about 19% DMSO. In each freezing vial, approximately $10^6$ cells of each clone were suspended in 0.25 ml of the freezing medium and cooled to $-80°$ C. at the rate of 1.0° C./min. Cells stored in liquid nitrogen were recovered by rapid thawing and seeding into pre-warmed medium at a cell density of $1-5 \times 10^5$/ml.

Growth In Culture and as Ascites Tumors

Information on the growth charcteristics of each clone was obtained by seeding clones in T-75 flasks in SDMEM supplemented with 2% rabbit serum. Cell number was determined using a particle counter interfaced to a pulse height analyzer. The doubling times for the hybrid cells grown in SDMEM with 2% RS were 48 hours for the HB8160 cells, 24 hours for the HB8159 cells, 24 hours for the HB8162 cells and 40 hours for the HB8161 cells.

For ascites growth, Balb/c mice were injected twice with 0.2 ml pristane at an interval of one week and irradiated with approximately 600 R of 1 MeV x-rays one day after the second pristane injection and approximately 10⁷ hybridoma cells were injected IP. Typically, the mice began to die from the resulting tumors 6-8 days after injection. At this time, the group of animals was sacrificed and the peritoneal cavities washed with about 20 ml of sterile phosphate-buffered saline (PBS). Viable sterile tumor cells were recovered for reinjection into additional animals.

Assay Procedures

Red cell agglutination activity was tested semi-quantitatively on slides. Serum diluted with PBS was mixed with an equal volume of a 10% (v/v) suspension of washed red cells in PBS. The rate and extent of agglutination was judged relative to the standard commercial anti-M and anti-N typing sera.

Two ELISA-based methods were used. The first employs whole red cells as the immobilized antigen, while the second uses purified glycophorin A. The whole-cell assay is based on methods known in the art. Briefly, 96-well microtiter plates were coated with poly-L-lysine by incubating 100 $\mu$l/well of a 50 $\mu$g/ml solution of poly-L-lysine at room temperature for 60 minutes. The wells were washed twice with PBS and then seeded with 10⁶ freshly obtained, washed erythrocytes by adding 100 $\mu$l of a 1:1000 dilution of packed cells in PBS. The cells were allowed to settle for 60 minutes at room temperature and then centrifuged for about 2 minutes at 500×g. The cells were immobilized by carefully pipeting 100 $\mu$l/well of a 0.025% glutaraldehyde (Eastman Kodak, Rochester, NY) solution in PBS and incubating for 30 minutes at room temperature. The plates were then washed three times with PBS and stored overnight at 4° C. with 200 $\mu$l/well of PBS containing 0.2% gelatin and 0.01% sodium azide. Following three washings with PBS, 25-100 $\mu$l of culture media or ascites fluid diluted in PBS was added per well and incubated for 60 minutes at 37° C. and for 60 minutes at room temperature (approximately 25° C.) The plates were then carefully washed 8 times with PBS containing 0.2% gelatin and 0.05% Tween 80 (PBS-G-T) followed by two washes with PBS. 100 $\mu$l/well of alkaline phosphatase-conjugated rabbit anti-mouse IgG (immunoglobulin G) (Cappel Laboratories, Cochranville, PA), diluted 1:300 in PBS-G-T was then added and incubated for 30 minutes at 37° C. and for 30 minutes at room temperature. The plates were again carefully washed 8 times with PBS-G-T and finally twice with 0.15M NaCl to remove phosphate which inhibits the enzyme reaction with colorimetric substrate. 100 $\mu$l/well of alkaline phosphatase p-nitrophenyl phosphate (Sigma Chemicals, St. Louis, MO) solution (1 mg/ml freshly prepared in a pH 9.6, 50 mM sodium bicarbonate-carbonate buffer containing 1 mM MgCl₂) was added and the plates incubated at 37° C.

The purified-antigen procedure was also adapted from methods known in the art. Antigen, either purified glycophorin A or Bovine Serum Albumen (BSA) (Gibco, Santa Clara, CA) at a concentration of 10 $\mu$g/ml was dissolved in a pH 9.6, 30 mM sodium-bicarbonate-carbonate buffer. 100 $\mu$l aliquots/well were added to Dynatech "Immulon 2" 96-well microtiter plates and incubated overnight at 4° C. These treated plates bind significantly more antigen than do the "Immulon 1" Dynatech plates and provide a sensitivity approximately equal to the whole red cell assay. Excess antigen was shaken out and the plates washed three times with PBS. 200 $\mu$l/well of PBS at pH 9.0 and containing 1% BSA was then added and the plates incubated for 30 minutes at room temperature. Following three washings with PBS, culture medium or ascites fluid diluted in PBS, was added in 25-100 $\mu$l aliquots and incubated for 60 minutes at 37° C. and for 60 minutes at room temperature. The plates were then carefully washed eight times with 0.05% Triton X-100 (Sigma Chemicals, St. Louis, MO) and twice with distilled water. Alkaline phosphatase-conjugated rabbit anti-mouse IgG (Cappel Laboratories, Cochranville, PA) was then added as described previously for whole red cell assay. Following washing eight times with 0.05% Triton X-100 and twice with distilled water, the enzyme substrate solution was added and the plates developed as described previously.

For analysis of enzyme activity, the plates were scanned using a Titertek Multiskan 96-well microtiter plate reader (Flow Laboratories, Inglewood, CA). Absorbence measurements at 405 nm were recorded as a function of time in a PDP 11/34 computer hard-wired to the reader. Slopes of OD 405/hr were calculated using linear regression analysis of the time points that closely fit a straight line. Linear data were usually obtained for optical densities less than 2 for times up to about 2 hours.

Antibody Binding to Erythrocyte Ghost Proteins

Specificity of binding of the antibodies only to glycophorin A was confirmed using an indirect immunoprecipitation assay. Purified aliquots of the monoclonal antibodies were incubated with Sepharose CL-4B Protein A beads (Pharmacia Five Chemicals, Piscataway, NJ). The resulting complex of the antibody IgG on the beads was then incubated with a red cell membrane solution containing all of the erythrocyte membrane-associated protein which was prepared by solubilizing washed red cell ghosts in a buffer containing 1% sodium deoxycholate. The beads were then washed and the antigen-antibody complexes dissociated from the beads by the addition of buffer containing 2% sodium dodecasulphate (SDS) and 2% $\beta$-mercaptoethanol and incubating the mixture in a boiling water bath for two minutes. The resulting supernatants were then analyzed on 10% sodium dodecasulphate polyacrylamide gel electrophoresis (SDS-PAGE). Staining with periodic acid schiff (PAS) and Coomassie Blue revealed specific binding of protein whose mobility corresponded only to the PAS-1 and PAS-2 dimer and monomer bands of glycophorin A.

Cell lines HB8160 and HB8159 are capable of producing antibodies which are specific only to glycophorin $A^M$. Cell line HB8161 is capable of producing antibodies specific only to glycophorin $A^N$. Cell line HB8162 is capable of producing antibodies which react with both glycophorin $A^M$ and $A^N$.

The particular embodiment was chosen and described in order to best explain the principles of the invention and its practical applications to thereby enable others skilled in the art to best utilize the invention in various embodiments and with various modifications as are suited to the particular use contemplated and is not to be construed as limiting in its application. It is intended that the scope of the invention be defined by the claims appended hereto.

We claim:

1. A hybridoma selected from the group consisting of HB 8159, HB 8160, HB 8161 and HB 8162.

2. A monoclonal antibody produced by a hybridoma selected from the group consisting of HB 8159, HB 8160, HB 8161, and HB 8162.

* * * * *